(12) United States Patent  
Kisner

(10) Patent No.: US 10,203,310 B2  
(45) Date of Patent: Feb. 12, 2019

(54) CHEMICAL DETECTION OF SUBSTANCES BY UTILIZING A SAMPLE MEDIUM IMPREGNATED WITH SOLID TEST CHEMICALS

(71) Applicant: DETECTACHEMN LLC, Houston, TX (US)

(72) Inventor: Travis Kisner, Sugar Land, TX (US)

(73) Assignee: DETECTACHEM LLC, Stafford, TX (US)

( * ) Notice: Subject to any disclaimer, the term of this patent is extended or adjusted under 35 U.S.C. 154(b) by 280 days.

(21) Appl. No.: 14/776,967

(22) PCT Filed: Mar. 17, 2014

(86) PCT No.: PCT/US2014/030467  
§ 371 (c)(1),  
(2) Date: Sep. 15, 2015

(87) PCT Pub. No.: WO2014/145663  
PCT Pub. Date: Sep. 18, 2014

(65) Prior Publication Data  
US 2016/0041134 A1 Feb. 11, 2016

Related U.S. Application Data

(60) Provisional application No. 61/800,177, filed on Mar. 15, 2013.

(51) Int. Cl.  
*G01N 31/22* (2006.01)  
*G01N 21/78* (2006.01)  
(Continued)

(52) U.S. Cl.  
CPC ............. *G01N 31/22* (2013.01); *D21H 19/14* (2013.01); *D21H 27/08* (2013.01); *G01N 21/78* (2013.01); *Y10T 436/173076* (2015.01)

(58) Field of Classification Search  
CPC ........ D21H 19/14; D21H 21/08; D21H 27/08; G01N 31/22; G01N 21/77; G01N 21/78; (Continued)

(56) References Cited

U.S. PATENT DOCUMENTS

| 3,511,608 A | * | 5/1970 | Anderson | ............. G01N 31/22 422/421 |
| 3,713,779 A |   | 1/1973 | Sirago et al. | |

(Continued)

FOREIGN PATENT DOCUMENTS

| EP | 1 766 361 A1 | 3/2007 |
| WO | WO-2008-044043 A1 | 4/2008 |

(Continued)

OTHER PUBLICATIONS

International Search Report and Written Opinion for PCT/US2014/030467, dated Sep. 24, 2014.

(Continued)

*Primary Examiner* — Maureen Wallenhorst  
(74) *Attorney, Agent, or Firm* — Winstead PC

(57) ABSTRACT

In some embodiments, the present disclosure pertains to substance detecting assemblies that include: (1) a sample medium (e.g., filter paper); and (2) a solid test chemical (e.g., zinc) impregnated with the sample medium. In some embodiments, the present disclosure pertains to methods of A making an assembly for detecting a substance by: (1) providing a sample medium; (2) providing a solid test chemical; and (3) impregnating the sample medium with the solid test chemical. In further embodiments, the present disclosure pertains to methods for detecting a substance by: (1) collecting the substance on a sample medium that is impregnated with a solid test chemical; and (2) initiating a reaction of the substance with the solid test chemical on the sample medium to generate a color that corresponds to the (Continued)

substance. In some embodiments, the sample medium is then inserted into a chemical detection unit for the detection of the substance.

36 Claims, 3 Drawing Sheets

(51) Int. Cl.
*D21H 19/14* (2006.01)
*D21H 27/08* (2006.01)

(58) Field of Classification Search
CPC .................. G01N 33/20; Y10T 436/17; Y10T 436/170769; Y10T 436/173076; Y10T 436/173845; Y10T 436/19; Y10T 436/206664
USPC ... 436/73, 81, 106, 107, 110, 111, 124, 135, 436/164, 165, 166, 167, 169; 422/400–404, 411, 413, 418, 419, 420, 422/430, 69, 82.09, 88
See application file for complete search history.

(56) References Cited

U.S. PATENT DOCUMENTS

| | | | |
|---|---|---|---|
| 4,061,468 A * | 12/1977 | Lange | G01N 33/521 162/140 |
| 4,673,657 A | 6/1987 | Christian | |
| 4,855,240 A | 8/1989 | Rosenstein et al. | |
| 4,857,453 A | 8/1989 | Ullman et al. | |
| 4,918,025 A | 4/1990 | Grenner | |
| 4,943,522 A | 7/1990 | Eisinger et al. | |
| 4,960,691 A | 10/1990 | Gordon et al. | |
| 4,965,047 A | 10/1990 | Hammond | |
| 5,006,474 A | 4/1991 | Horstman et al. | |
| 5,110,552 A | 5/1992 | Guigan | |
| 5,154,888 A | 10/1992 | Zander et al. | |
| 5,480,612 A | 1/1996 | Margalit | |
| 5,516,488 A | 5/1996 | Bunce et al. | |
| 5,648,047 A | 7/1997 | Kardish et al. | |
| 5,652,149 A | 7/1997 | Mileaf et al. | |
| 5,679,584 A | 10/1997 | Mileaf et al. | |
| 5,798,215 A | 8/1998 | Cathey et al. | |
| 5,859,375 A | 1/1999 | Danylewych-May et al. | |
| 6,077,711 A | 6/2000 | Singer | |
| 6,146,589 A | 11/2000 | Chandler | |
| 6,228,657 B1 | 5/2001 | Genovese et al. | |
| 6,426,230 B1 | 7/2002 | Feistel | |
| 6,540,962 B1 | 4/2003 | Okubo et al. | |
| 6,582,970 B1 | 6/2003 | Manita | |
| 6,673,628 B2 | 1/2004 | Freitag et al. | |
| 6,689,317 B1 | 2/2004 | Rees | |
| D502,655 S | 3/2005 | Huang | |
| 7,036,388 B1 | 5/2006 | Genovese et al. | |
| 7,086,277 B2 | 8/2006 | Tess et al. | |
| 7,132,078 B2 | 11/2006 | Rawson et al. | |
| 7,189,522 B2 | 3/2007 | Esfandiari | |
| 7,267,799 B1 | 9/2007 | Borich et al. | |
| 7,294,306 B2 | 11/2007 | Haas et al. | |
| 7,384,599 B2 | 6/2008 | Brewer | |
| 7,445,753 B1 | 11/2008 | Kreis et al. | |
| 7,695,975 B2 * | 4/2010 | Bukhtiyarov | G01N 33/52 422/50 |
| 7,807,104 B2 | 10/2010 | Haas et al. | |
| 7,867,445 B1 | 1/2011 | Haas et al. | |
| 7,939,029 B2 | 5/2011 | Eckels et al. | |
| 8,293,188 B2 | 10/2012 | Bukhtiyarov et al. | |
| 8,435,462 B2 | 5/2013 | Bedingham et al. | |
| 8,669,115 B2 | 3/2014 | Pagoria et al. | |
| D714,171 S | 9/2014 | Hoofnagle et al. | |
| 8,845,978 B2 | 9/2014 | Johnson | |
| 8,980,641 B2 | 3/2015 | Clift et al. | |
| D727,762 S | 4/2015 | Kisner et al. | |
| 9,250,189 B1 | 2/2016 | Johnson | |
| 2002/0142301 A1 | 10/2002 | Hovig et al. | |
| 2002/0187076 A1 | 12/2002 | DiCesare et al. | |
| 2003/0129767 A1 | 7/2003 | Bautista et al. | |
| 2004/0224354 A1 | 11/2004 | Kambara et al. | |
| 2005/0092063 A1 | 5/2005 | Tajima et al. | |
| 2005/0101027 A1 | 5/2005 | Haas | |
| 2005/0181517 A1 | 8/2005 | Chandler et al. | |
| 2006/0092030 A1 | 5/2006 | Povenmire | |
| 2006/0292040 A1 | 12/2006 | Wickstead et al. | |
| 2008/0182334 A1 | 7/2008 | Amisar | |
| 2009/0325300 A1 | 12/2009 | Clift et al. | |
| 2010/0014085 A1 | 1/2010 | Sekimoto | |
| 2010/0203578 A1 | 8/2010 | Geiger et al. | |
| 2010/0229633 A1 | 9/2010 | Pagoria et al. | |
| 2010/0291588 A1 | 11/2010 | McDevitt et al. | |
| 2011/0081723 A1 | 4/2011 | Miller et al. | |
| 2013/0343645 A1 | 12/2013 | Dalal et al. | |
| 2014/0127824 A1 * | 5/2014 | Amisar | G01N 21/78 436/107 |
| 2014/0314625 A1 | 10/2014 | Clift et al. | |
| 2014/0322816 A1 | 10/2014 | Haas et al. | |
| 2015/0268171 A1 * | 9/2015 | Haber | G01N 21/78 436/110 |
| 2015/0290638 A1 | 10/2015 | Kisner et al. | |

FOREIGN PATENT DOCUMENTS

| | | |
|---|---|---|
| WO | WO-2008-097268 A2 | 8/2008 |
| WO | WO-2012-119128 A1 | 9/2012 |
| WO | WO-2014-081460 A1 | 5/2014 |

OTHER PUBLICATIONS

International Preliminary Report on Patentability for PCT/US2014/030467, dated Sep. 24, 2015.
Dexter McRae, Wallace Haywood, Jonathan Powell, and Betty Harris. Jan. 1995. "High Explosive Spot Test Analyses of. Samples from Operable Unit (OU) 1111." UC-902 and UC-901. Los Alamos National Laboratories.

* cited by examiner

CHEMICAL DETECTION OF SUBSTANCES BY UTILIZING A SAMPLE MEDIUM IMPREGNATED WITH SOLID TEST CHEMICALS

CROSS-REFERENCE TO RELATED APPLICATIONS

This application claims priority to U.S. Provisional Patent Application No. 61/800,177, filed on Mar. 15, 2013. The entirety of the aforementioned application is incorporated herein by reference.

This application is related to U.S. patent application Ser. No. 12/309,704, filed on Jan. 26, 2009, now U.S. Pat. No. 8,980,641; PCT/US2013/032603, filed on Mar. 15, 2013; and U.S. patent application Ser. No. 29/475,778, filed on Dec. 6, 2013, now U.S. D727776 D727762. The entirety of each of the aforementioned applications is also incorporated herein by reference.

STATEMENT REGARDING FEDERALLY SPONSORED RESEARCH

Not applicable.

BACKGROUND

Methods and systems for the trace detection of various substances (e.g., drugs and explosives) suffer from numerous limitations. Such limitations include efficacy, sensitivity, and the availability of test chemicals. Various embodiments of the present disclosure address these limitations.

SUMMARY

In some embodiments, the present disclosure pertains to assemblies for detecting a substance. In some embodiments, the assemblies include: (1) a sample medium; and (2) a solid test chemical that is impregnated with the sample medium. In some embodiments, the solid test chemical is dispersed on a surface of the sample medium. In some embodiments, the solid test chemical is selected from the group consisting of metals, transition metals, metalloids, and combinations thereof. In some embodiments, the solid test chemical is zinc.

In some embodiments, the sample medium is selected from the group consisting of filter papers, porous sheets of fibers, porous papers, and combinations thereof. In some embodiments, the sample medium comprises a pad of a flexible card component that can be inserted into a chemical detection unit.

Additional embodiments of the present disclosure pertain to methods of making an assembly for detecting a substance. In some embodiments, such methods comprise: (1) providing a sample medium; (2) providing a solid test chemical; and (3) impregnating the sample medium with the solid test chemical. In some embodiments, the impregnating occurs by: (1) suspending the solid test chemical in a solvent to form a suspension; (2) applying the suspension onto the sample medium; and (3) allowing the solvent to evaporate.

In further embodiments, the present disclosure pertains to methods for detecting a substance by: (1) collecting the substance on a sample medium that is impregnated with a solid test chemical; and (2) initiating a reaction of the substance with the solid test chemical on the sample medium to generate a color that corresponds to the substance.

In some embodiments, the substance to be detected is selected from the group consisting of biohazards, toxins, radioactive materials, narcotics, explosives, and combinations thereof. In some embodiments, the substance to be detected includes one or more explosives, such as nitroaromatics, nitrate esters, nitramines, inorganic nitrates, chlorates, peroxides, perchlorates, and combinations thereof.

In some embodiments, the solid test chemical is zinc, and the substance to be detected is an inorganic nitrate. In some embodiments, the zinc reacts with the inorganic nitrate to produce nitrite ions. The nitrite ions can then undergo a subsequent reaction (e.g., a Greiss reaction) to generate a color.

In some embodiments, the substance is collected on the sample medium by swiping the sample medium onto a surface containing the substance. In some embodiments, the sample medium is a pad of a flexible card component that is subsequently inserted into a chemical detection unit for automatic colorimetric detection of the substance.

DESCRIPTION OF THE FIGURES

FIG. 1A provides an image of a sample medium 10 that is impregnated with solid test chemicals. FIG. 1B provides an image of sample medium 10 as part of flexible card component 12. FIG. 1C provides an image of the various parts of flexible card component 12.

DETAILED DESCRIPTION

Figure 1:
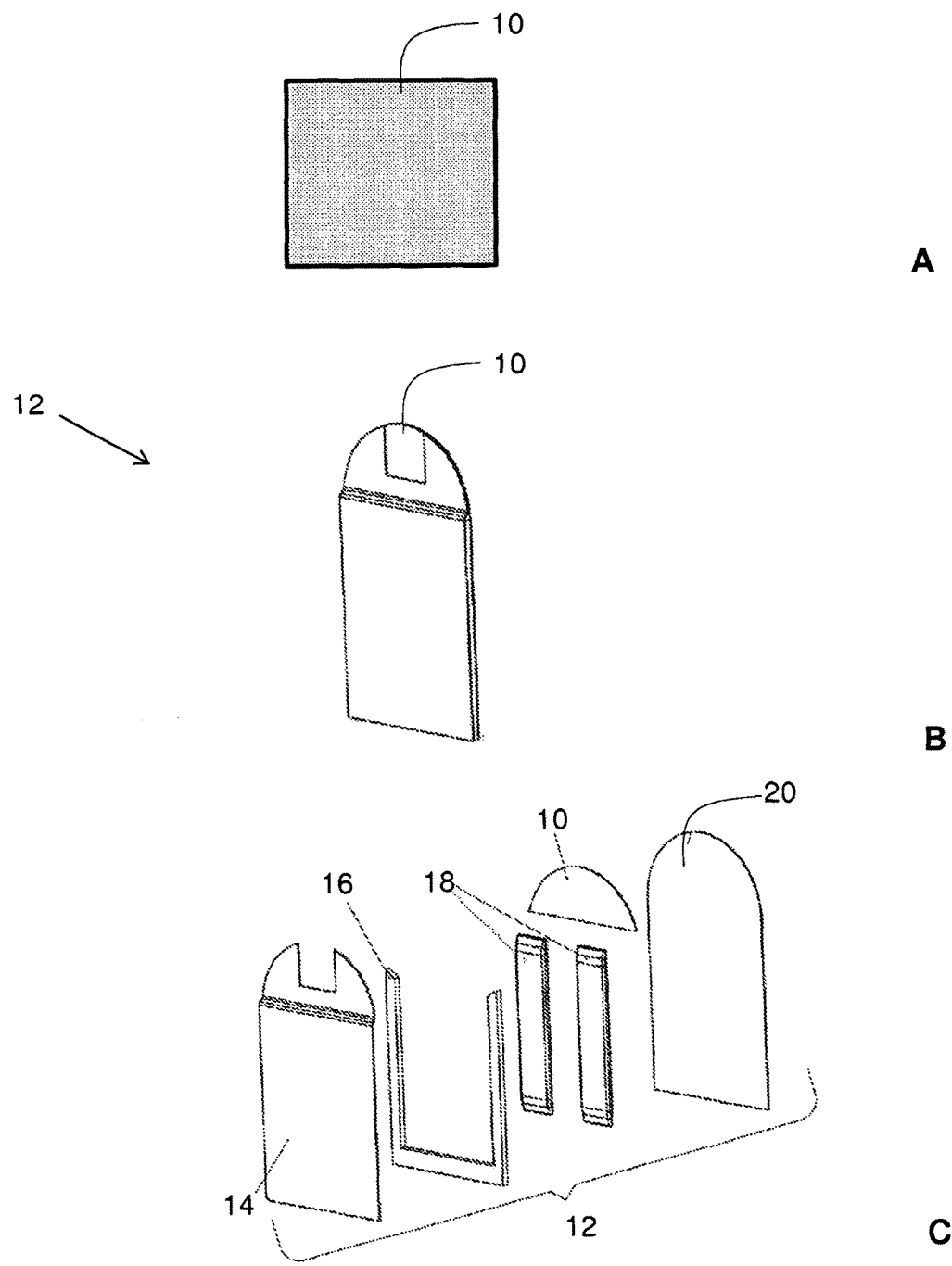
FIG. 1 provides images of a sample medium in various contexts.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Chemical detection systems and methods are known to be useful for detecting various substances, such as explosives and drugs. In many instances, chemical detection systems and methods involve use of test chemicals that react with the substance to produce a measurable or observable product for detection of the substance. For example, colorimetric chemical detection systems and methods detect the substance by producing a colored product for detection of the substance. Conventional detection methods and systems tend to use suspension of the test chemicals in a liquid.

For detection of some substances, it is desirable to have solids or metals involved in a chemical reaction. For example, zinc is known to react with inorganic nitrates to reduce them to nitrite ions that react with further test chemical for detection. For example, the Griess reaction is well-known for producing a colored azo dye from reaction of test chemicals with nitrite ions. However, zinc is not soluble in liquids. Therefore, it is suspended in suitable solvents for colorimetric testing.

Nonetheless, a difficulty arises in getting insoluble solids to mix well in solution. More particularly, it tends to be difficult to be able to keep the solids suspended without constant stirring. Furthermore, any dispensing of the solid in solution is challenging due to the dispensing method used.

Therefore, there remains a need for systems and processes through which to utilize solid test chemicals efficiently and effectively. More particularly, various methods and systems are desirable to allow solid test chemicals to interact with various substances without the need to suspend them in a liquid.

In some embodiments, the present disclosure pertains to assemblies that are impregnated with solid test chemicals for detecting various substances. In some embodiments, the present disclosure pertains to methods of making such assemblies. In some embodiments, the present disclosure pertains to using such assemblies for detecting substances.

Detection Assemblies

In some embodiments, the present disclosure pertains to assemblies for detecting various substances. In some embodiments that are described in more detail herein, the substances to be detected include, without limitation, biohazards, toxins, radioactive materials, narcotics, explosives, and combinations thereof.

In some embodiments, the assemblies include a sample medium that is impregnated with a solid test chemical. As set forth in more detail herein, the detection assemblies of the present disclosure can include various sample media and solid test chemicals.

Sample Media

A sample medium generally refers to a region, structure or system component that can be used to detect a substance. In some embodiments, the sample medium includes, without limitation, filter papers, porous sheets of fibers, porous papers, and combinations thereof. In some embodiments, the sample medium is a filter paper. Various types of materials may also be used as sample media. For instance, in some embodiments, the materials in the sample medium include, without limitation, papers, polyesters, cotton, plastics, and combinations thereof. In more specific embodiments, the sample medium includes at least one of a cotton-based filter paper, a polyester-based filter paper, a plastic-based filter paper, and combinations thereof.

In some embodiments, the sample medium is in the form of a pad. For instance, in some embodiments, a sample medium is in the form of pad 10 shown in FIG. 1A. In some embodiments, the sample medium is in the form of a pad of a flexible card component. For instance, in some embodiments that are shown in FIG. 1B, the sample medium is in the form of pad 10 on flexible card component 12.

In some embodiments, the sample medium may be in fluid communication with one or more liquid reagents. For instance, in some embodiments shown in FIG. 1C, the sample medium may be in the form of pad 10 of flexible card component 12, where the flexible card component contains two reagent releasable capsules 18 that are in fluid communication with pad 10. In this embodiment, flexible card component 12 also contains top layer 14, inner layer 16, and bottom layer 20.

Additional structures for establishing fluid communication between a sample medium and one or more liquid reagents can also be envisioned. For instance, in some embodiments, the sample media of the present disclosure may be used on the card pads described in U.S. patent application Ser. No. 12/309,704, filed on Jan. 26, 2009, now U.S. Pat. No. 8,980,641. In further embodiments, the sample media of the present disclosure may be utilized in the test areas described in PCT/US2013/032603.

Solid Test Chemicals

In some embodiments, the sample medium is associated with a solid test chemical. Solid test chemicals generally refer to materials that are in solid form and capable of reaction with a substance to be detected (e.g., explosives). Various solid test chemicals may be associated with sample media. For instance, in some embodiments, the solid test chemical includes, without limitation, metals, transition metals, metalloids, and combinations thereof. In some embodiments, the solid test chemical includes, without limitation, nickel, titanium, vanadium, manganese, iron, cobalt, copper, zinc, molybdenum, gold, silver, and combinations thereof. In some embodiments, the solid test chemical is zinc.

In some embodiments, the solid test chemical is insoluble in water. In some embodiments, the solid test chemical is insoluble in various solvents, such as ethanol.

Solid test chemicals may be associated with sample media in various manners. For instance, in some embodiments the sample medium is impregnated with a solid test chemical. In some embodiments, the solid test chemical is dispersed on a surface of the sample medium. In some embodiments, the solid test chemical is localized on a selected region of the sample medium. In some embodiments, the solid test chemical is dispersed uniformly on the surface of the sample medium.

Methods of Making Chemical Detection Assemblies

In some embodiments, the present disclosure pertains to methods of making an assembly for detecting a substance. In some embodiments, the assembly methods include: (1) providing a sample medium; (2) providing a solid test chemical; and (3) impregnating the sample medium with the solid test chemical. Various sample media and solid test chemicals (as described previously) may be utilized for the aforementioned assembly methods. Furthermore, various methods may be utilized to impregnate sample media with solid test chemicals.

Impregnating Sample Media with Solid Test Chemicals

In some embodiments, sample media are impregnated with solid test chemicals by applying solid test chemicals onto sample media. In some embodiments, the applying occurs by spraying, dropping, chemical vapor deposition, sputtering, and similar methods.

In more specific embodiments, sample media are impregnated with solid test chemicals by: (1) suspending the solid test chemical in a solvent to form a suspension; (2) applying the suspension onto the sample medium; and (3) allowing the solvent to evaporate. In some embodiments, the suspending occurs by mixing the solid test chemical into a solvent. In some embodiments, the applying occurs by spraying the suspension onto the sample medium. In some embodiments, the applying occurs by dropping the suspension onto the sample medium. In some embodiments, the applying includes removing predetermined volumes from a continuously stirring suspension and dropping the suspension onto the sample medium.

In some embodiments, the solvent is allowed to evaporate by incubation at room temperature. In some embodiments, the solvent is inert to the reaction between the solid test chemical and the substance. In some embodiments, the solvent includes, without limitation, ethanol, methanol, isopropyl alcohol, water, and combinations thereof. In some embodiments, the solvent is ethanol.

Methods of Detecting Substances

Figure 2:
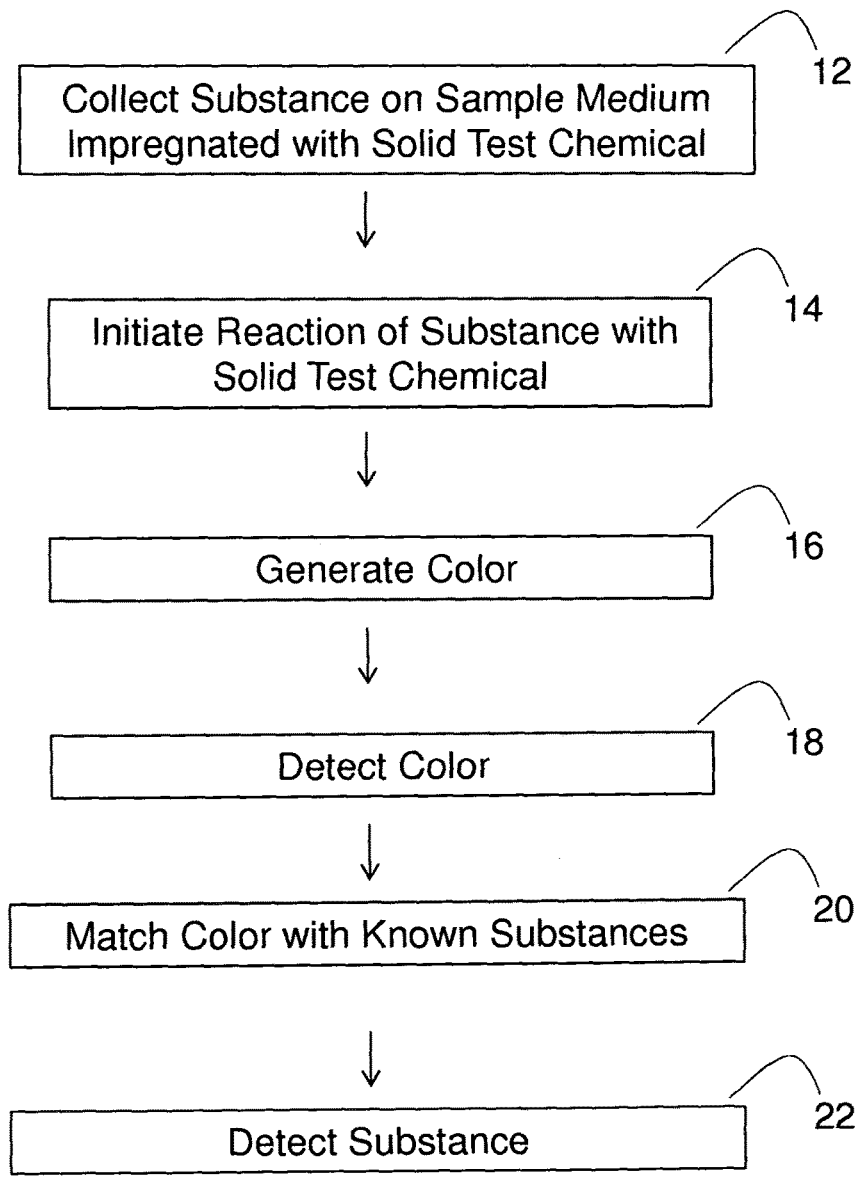
FIG. 2 provides a scheme for the use of a sample medium for detecting substances.

Additional embodiments of the present disclosure pertain to methods of detecting a substance by utilizing the sample media of the present disclosure. For instance, in some embodiment illustrated in FIG. 2, such methods include: collecting the substance on a sample medium that is impregnated with a solid test chemical (step 12); and initiating a reaction of the substance with the solid test chemical on the sample medium (step 14) to generate a color that corresponds to the substance (step 16). In some embodiments, the methods of the present disclosure also include one or more steps of detecting the color (step 18), matching the color to known substances (step 20), and/or detecting the substance (step 22).

As set forth in more detail herein, the methods of the present disclosure can have various embodiments. In particular, various test chemicals may be impregnated onto various sample media to react with various substances on the sample media. Furthermore, various methods may be utilized to collect substances on sample media, initiate reactions, and generate colors.

In some embodiments, one or more of the aforementioned steps may occur in an automated and/or controlled manner. In some embodiments, one or more of the aforementioned steps may occur by the utilization of a chemical detection unit.

Sample Media

As set forth previously, the methods of the present disclosure may utilize various sample media. In some embodiments, the sample medium includes, without limitation, filter papers, porous sheets of fibers, porous papers, and combinations thereof. In some embodiments, the sample medium includes at least one of a cotton-based filter paper, a polyester-based filter paper, a plastic-based filter paper, and combinations thereof.

In some embodiments, the sample medium is in the form of a pad, such as pad 10 shown in FIG. 1A. In some embodiments, the sample medium is in the form of a pad of a flexible card component, such as pad 10 on flexible card component 12, as shown in FIG. 1B. In some embodiments, the sample medium may be in fluid communication with one or more liquid reagents, such as liquid reagents in reagent releasable capsules 18 of flexible card component 12, as shown in FIG. 1C.

Solid Test Chemicals

As set forth previously, various solid test chemicals may be impregnated onto various sample media. In some embodiments, the solid test chemicals are dispersed on a surface of a sample medium. In some embodiments, the solid test chemicals include, without limitation, metals, transition metals, metalloids, and combinations thereof. In some embodiments, the solid test chemical includes, without limitation, nickel, titanium, vanadium, manganese, iron, cobalt, copper, zinc, molybdenum, gold, silver, and combinations thereof. In some embodiments, the solid test chemicals may include zinc.

Substances

The methods of the present disclosure may be utilized to detect various substances. In some embodiments, the substances may include, without limitation, biohazards, toxins, radioactive materials, narcotics, explosives, and combinations thereof.

In some embodiments, the substance to be detected includes explosives. In some embodiments, the explosives include, without limitation, nitroaromatics, nitrate esters, nitramines, inorganic nitrates, chlorates, peroxides, perchlorates, and combinations thereof.

In some embodiments, the explosives include inorganic nitrates, such as ammonium nitrate, urea nitrate, potassium nitrate, sodium nitrate, and the like. In some embodiments, the explosives include nitroaromatics, such as TNT, TNB, DNT, DNB, Tetryl, and the like. In some embodiments, the explosives include nitrate esters and nitramines, such as HMX, RDX, PETN, Semtex, Nitroglycerin, EGDN, Pyrodex, and the like. In some embodiments, the explosives include chlorates, such as sodium chlorate, potassium chlorate, and the like. In some embodiments, the explosives include peroxides, such as TATP, HMTD, and the like. The detection of additional explosives can also be envisioned.

In more specific embodiments, zinc is the solid test chemical and the substance is an inorganic nitrate. In further embodiments, zinc is used as a solid test chemical to detect ammonium nitrate, urea nitrate, potassium nitrate, sodium nitrate, and combinations thereof.

In some embodiments, substances to be detected include narcotics. In some embodiments, the narcotics include, without limitation, opiates, cocaine, methamphetamine, MDMA, ecstasy, THC, marijuana, ketamine, and combinations thereof. In some embodiments, the narcotics include opiates, such as heroin, morphine, codeine, and the like. The detection of additional narcotics can also be envisioned.

Substances may be present on a sample medium in various amounts. For instance, in some embodiments, a substance may be present on a sample medium in amounts ranging from about 10 ng to about 100 mg. In some embodiments, a substance may be present on a sample medium in amounts ranging from about 100 ng to about 1 mg. In some embodiments, several substances may be present on a sample medium in total amounts ranging from about 10 ng to about 100 mg. In some embodiments, several substances may be present on a sample medium in total amounts ranging from about 100 ng to about 1 mg.

In addition, substances may be present on a sample medium in various states. For instance, in some embodiments, substances may be present on a sample medium in solid state, liquid state, gaseous state, or combinations of such states. In some embodiments, substances may be present on a sample medium in a solid state. In some embodiments, substances may be present on a sample medium in a liquid state.

Collection of Substances

Various methods may also be utilized to collect substances on sample media. For instance, in some embodiments, a substance may be collected on a sample medium by swiping the sample medium onto a surface that contains the substance. In some embodiments, a substance is collected on a sample medium by dropping a liquid containing the substance onto the sample medium. In some embodiments, a substance is collected on a sample medium by exposing the sample medium to a gaseous environment containing the substance. Additional methods of collecting substances on sample media can also be envisioned.

Reaction Initiation

Various methods may also be utilized to initiate a reaction of a substance with a solid test chemical on a sample medium. In some embodiments, the reactions of substances with solid test chemicals may be initiated manually. In some embodiments, the reactions of substances with solid test chemicals may be initiated in an automated and/or controlled fashion. In some embodiments, a chemical detection unit may be utilized to initiate reactions of substances with solid test chemicals. Various aspects of such embodiments are described in more detail herein For instance, in some embodiments, the reaction may be initiated by incubating the sample medium that contains a substance and solid test chemical at room temperature. In some embodiments, the sample medium is incubated at room temperature for about 5 minutes to about 60 minutes.

In some embodiments, a reaction of a substance with a solid test chemical is initiated by applying one or more liquid reagents onto the sample medium. In some embodiments, a reaction is initiated by utilizing a flexible card component that includes a sample medium and at least one liquid reagent in a reagent releasable capsule. For instance, in some embodiments where a substance is on pad 10 of flexible card component 12 (FIG. 1C), liquid reagents from reagent releasable capsules 18 may be applied to pad 10 in order to initiate the reaction of the substance with a solid test chemical on pad 10.

In some embodiments, the reaction is initiated after coupling a sample medium with a hand held chemical detection unit. In more specific embodiments shown in FIG. 3, a reaction is initiated by coupling flexible card component 12 that contains pad 10 with chemical detection unit 100 through opening 30. The use of additional chemical detection units can also be envisioned. For instance, another chemical detection unit suitable for use with the methods of the present disclosure is disclosed in U.S. patent application Ser. No. 29/475,778, filed on Dec. 6, 2013, now U.S. D727762.

In some embodiments, the coupling of a flexible card component with a hand held chemical detection unit causes a wall of a reagent releasable capsule to yield to fluid flow to establish fluid communication between a liquid reagent in the reagent releasable capsule and the pad. For instance, in some embodiments illustrated in FIGS. 1C and 3, the coupling of flexible card component 12 with hand held chemical detection unit 100 causes walls of reagent releasable capsules 18 to yield to fluid flow to establish fluid communication between liquid reagents in reagent releasable capsules 18 and pad 10.

In some embodiments, establishment of fluid communication between at least one reagent releasable capsule and a pad can occur by a disruption of a wall of the reagent releasable capsule upon the coupling of the pad with a hand held chemical detection unit. In some embodiments, the disruption of the wall of the reagent releasable capsule occurs by at least one of an application of pressure to the wall, an application of heat to the wall, a mechanical breaking of the wall, a mechanical puncturing of the wall, or combinations thereof.

In some embodiments, the methods of the present disclosure also include a step of stimulating a reaction of a substance with a solid test chemical on a sample medium. In some embodiments, the stimulating occurs after initiating the reaction. In some embodiments, the stimulating occurs by heating the sample medium. In some embodiments, the stimulating occurs after applying one or more liquid reagents onto the sample medium.

Figure 3:
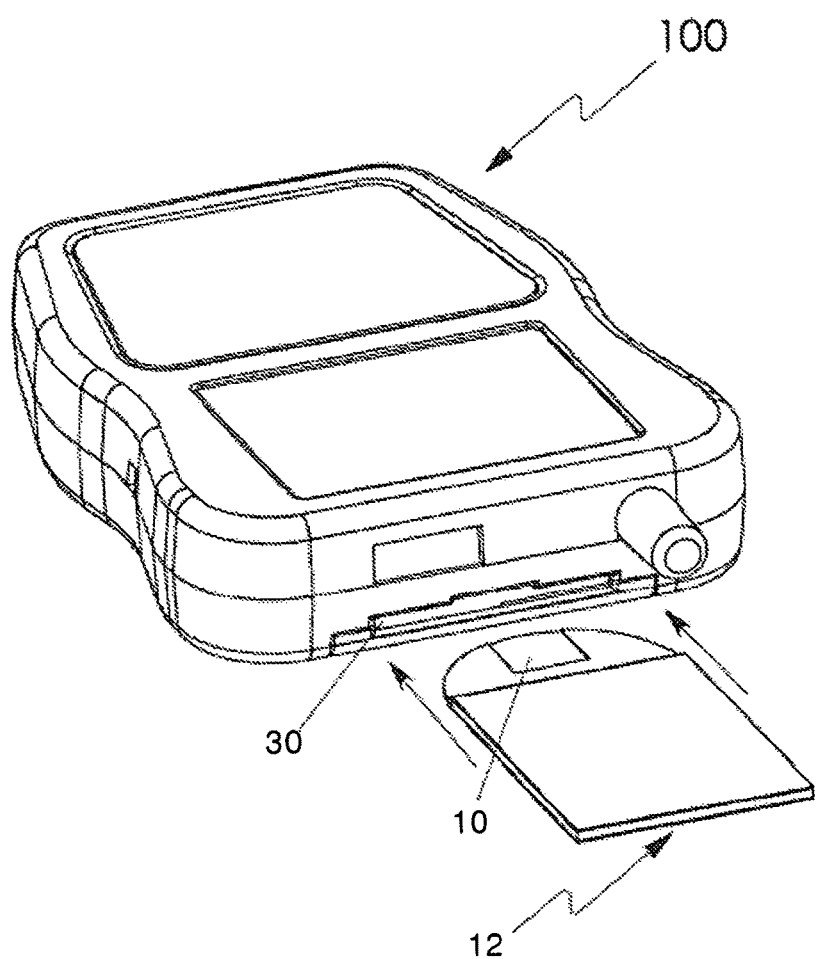
FIG. 3 provides an image of a chemical detection unit that can be utilized to detect substances on a sample medium.

In some embodiments, the stimulating occurs inside a hand held chemical detection unit, such as chemical detection unit 100 (FIG. 3). In some embodiments, the simulating generates a color that corresponds to the substance. In some embodiments, the stimulating includes an application of heat to the pad of a flexible card component (e.g., pad 10 of flexible card component 12, as shown in FIGS. 3 and 1A) to enhance the reaction.

Various liquid reagents may be utilized to initiate reactions of substances with solid test chemicals. For instance, in some embodiments, the liquid reagents may include one or more solvents. In some embodiments, the solvents may include, without limitation, ethanol, methanol, isopropyl alcohol, toluene, hexanes, water, various alcohols, acetonitrile, and combinations thereof.

Various reactions of substances with solid test chemicals may occur. In some embodiments, the solid test chemical serves as a reactant in a reaction. In some embodiments, the solid test chemical serves as a catalyst in a reaction. In more embodiments where the solid test chemical is zinc and the substance is an inorganic nitrate (e.g., ammonium nitrate, urea nitrate, potassium nitrate, sodium nitrate and combinations thereof), the zinc reacts with the inorganic nitrate to produce nitrite ions.

Generation of Color

In some embodiments, a color is generated upon the reaction of a solid test chemical with a substance. In some embodiments, the color is generated as a direct result of the reaction of a solid test chemical with a substance. In some embodiments, the color is generated as an indirect result of the reaction of a solid test chemical with a substance. For instance, in some embodiments, one or more additional reactions after the reaction of the solid test chemical with a substance may be required to generate a color. In a more specific embodiment where zinc is the solid test chemical and the substance includes inorganic nitrates (e.g., ammonium nitrate, urea nitrate, potassium nitrate, sodium nitrate and combinations thereof), the zinc reacts with inorganic nitrates to reduce them to nitrite ions. Thereafter, the nitrite ions react with one or more liquid reagents (e.g., reagents from reagent releasable capsules 18 shown in FIG. 1C) in a Griess reaction to produce a colored azo dye.

In some embodiments, the generated color is derived from regions of the human visible spectrum, ultraviolet regions of the electromagnetic spectrum, infrared regions of the electromagnetic spectrum, and combinations thereof. In some embodiments, the generated color includes a change in color that is different form the solid test chemical and the substance. In some embodiments, the color includes a change in a spectral pattern of colors that is different from the spectral pattern of colors of the solid test chemical and the substance.

Detection of Color

Various methods may be utilized to detect colors that are generated upon the reaction of a solid test chemical with a substance. In some embodiments, the generated color may be detected visually by the naked eye. In some embodiments, the generated color may be detected by utilizing an optical instrument. In some embodiments, the optical instrument may be in a hand held chemical detection unit, such as chemical detection unit 100 (FIG. 3). In some embodiments, the chemical detection unit may detect the color and store data related to the color.

In some embodiments, the chemical detection unit may contain an optical instrument that includes light emitting diodes and an optical sensor. In some embodiments, the light emitting diodes illuminate the sample medium with various colors of light to allow for detection of a spectral pattern of colors by the optical sensor.

Matching of the Generated Color with Known Substances

Various methods may also be utilized to match colors generated from the reaction of a solid test chemical with a substance (i.e., generated color) with known substances. For instance, in some embodiments, the matching occurs by matching the generated color with the generated color of known substances in a database to determine the substance in the sample. In some embodiments, the matching occurs manually. In some embodiments, the matching occurs automatically. In more specific embodiments, the matching includes analyzing data (e.g., stored data) related to the generated color. In some embodiments, the matching occurs by utilizing a comparison algorithm. In some embodiments, the matching occurs by analyzing data (e.g., stored data) related to the generated color by utilizing a comparison algorithm.

In some embodiments, the matching occurs by comparing the generated color to a certain color threshold value. In some embodiments, if the generated color exceeds the color threshold value, then a certain substance is detected (e.g., an explosive, such as an inorganic nitrate). However, if there generated color does not exceed the color threshold value, then the substance is not detected.

In some embodiments, the generated color is compared to a color threshold value by utilizing a color algorithm. In some embodiments, the color threshold value may include an algorithm that utilizes color magnitude or intensity, rate of color change, decreasing color change and timing of the various color changes.

In further embodiments, the methods of the present disclosure may also include a step of displaying detection results. For instance, in some embodiments, detection results are displayed on a display unit of a hand held chemical detection unit, such as chemical detection unit 100 (FIG. 3).

Control of Reactions

In some embodiments, the methods of the present disclosure may also include one or more control steps over reaction conditions. For instance, in some embodiments, the initiating of the reaction is performed in a controlled sequence of reactions with liquid reagents in at least a first reagent releasable capsule and a second reagent releasable capsule (e.g., reagent releasable capsules 18, as shown in FIG. 1A), where the first reagent releasable capsule and the second reagent releasable capsule are in fluid communication with the sample medium (e.g., pad 10 on flexible card component 12, as also shown in FIG. 1A). In more specific embodiments, the initiating of the reaction is controlled by controlling flow times of the liquid reagents in the first and second reagent releasable capsules onto the sample medium. For instance, in some embodiments, the controlling includes controlling flow rates of the liquid reagents in the first and second reagent releasable capsules onto the sample medium. In some embodiments, the controlling includes controlling the arrival of the liquid reagents in the first and second reagent releasable capsules onto the sample medium. In some embodiments, the controlling results in the arrival of the liquid reagent in the first reagent releasable capsule onto the sample medium prior to the arrival of the liquid reagent in the second reagent releasable capsule onto the sample medium. In some embodiments, the controlling results in the arrival of the liquid reagent in the second reagent releasable capsule onto the sample medium prior to the arrival of the liquid reagent in the first reagent releasable capsule onto the sample medium. In some embodiments, the controlling results in the simultaneous arrival of the liquid reagents in the first and second reagent releasable capsules onto the sample medium. Additional methods by which to control reaction conditions are described in PCT/US2013/032603.

Applications and Advantages

The methods and systems of the present disclosure allow for chemical reactions to take place that involve insoluble test chemicals, such as insoluble metals (e.g., zinc). Furthermore, the methods and systems of the present disclosure allow for the colorimetric detection of trace substances by utilizing such reactions.

To the best of Applicant's knowledge, the colorimetric detection of trace substances by utilizing solid test chemicals that are impregnated onto a sample medium has not been performed or deemed feasible. Moreover, such methods can be used for the automated detection of various trace substances in various environments, such as the detection of drugs and/or explosives at airports, public areas, and other environments. In some embodiments, the methods and systems of the present disclosure may be utilized to detect trace amounts of substances that are present on a sample medium in amounts ranging from about 10 ng to about 100 mg. In some embodiments, the methods and systems of the present disclosure may be utilized to detect trace amounts of substances that are present on a sample medium in amounts ranging from about 100 ng to about 1 mg.

The systems and methods of the present disclosure are suitable for use with various automated colorimetric detection systems. Examples of automated colorimetric detection systems are described in U.S. patent application Ser. No. 12/309,704, filed on Jan. 26, 2009, now U.S. Pat. No. 8,980,641; and PCT/US2013/032603, filed on Mar. 15, 2013. For instance, in some embodiments, the sample media of the present disclosure may be used on the card pads described in U.S. patent application Ser. No. 12/309,704, filed on Jan. 26, 2009, now U.S. Pat. No. 8,980,641. In further embodiments, the sample media of the present disclosure may be utilized in the test areas described in PCT/US2013/032603.

Additional Embodiments

Reference will now be made to more specific embodiments of the present disclosure. However, Applicant notes that the disclosure below is for illustrative purposes only and is not intended to limit the scope of the claimed subject matter in any way.

Example 1. Fabrication of Zinc Impregnated Sample Media

This example illustrates impregnation of zinc (Zn) on a sample medium. Various methods can be used to impregnate the Zn into a sample medium. The even, thorough and uniform distribution of Zn on a sample medium is an important factor for facilitating its consistent reaction with substances.

One way of impregnating zinc onto a sample medium is to mix it in a solvent while continually agitating it to keep the metal particles suspended. This suspension can then be applied to the sample medium. Methods to achieve this can be dipping the medium in the suspension, dripping the suspension, or spraying the suspension onto the medium. The first two methods are preferred as spraying a suspension with metal particles can be problematic due to the potential clogging of the sprayer.

A suspension of 0.25% Zn and ethanol (EtOH) was made by mixing 0.2 g of Zn with 79.1 g of EtOH to produce the metal suspension. 10 uL of the suspension was dispensed on the sample medium area (i.e., a porous filter paper) to form a uniform circle of aqueous suspension. Next, EtOH or other solvents were allowed to evaporate for 2-3 minutes, thereby leaving impregnated Zn on the sample medium.

The uniformity of the impregnated Zn on the medium is dependent on the flow and the coverage of the suspension. Rapid flow of the suspension throughout the target sample medium is optimal, as it distributes the Zn before it has a chance to settle out of the suspension.

With the test medium now impregnated with the metal, chemicals introduced to the medium will now utilize the presence of the metal to implement the colorimetric reaction to detect the presence of the substance under question.

Example 2. Detection of Substances

This example illustrates a specific method of utilizing flexible card component 12 (FIGS. 1A-B) and chemical detection unit 100 (FIG. 3) to detect an unknown substance by utilizing a sample medium that is impregnated with a solid test chemical (e.g., the zinc impregnated sample medium from Example 1). Pad 10 on flexible card component 12 represents a sample medium that is impregnated with a solid test chemical. Pad 10 is in fluid communication with reagent releasable capsules 18 of flexible card component 12 (FIG. 1C). In operation, pad 10 is swiped onto a surface of interest that is suspected of containing a substance. Next, a reaction between the substance and solid test chemical on the pad 10 is initiated by coupling flexible card component 12 with chemical detection unit 100 through opening 30. The coupling of flexible card component 12 with chemical detection unit 100 causes walls of reagent releasable capsules 18 to yield to fluid flow to establish fluid communication between liquid reagents in reagent releasable capsules 18 and pad 10. This can happen by a disruption of the walls of the reagent releasable capsules 18 upon the coupling of pad 10 with chemical detection unit 100.

The arrival of the liquid reagents from reagent releasable capsules 18 onto pad 10 results in the reaction of the solid test chemical with the substance. This in turn leads to the generation of a color.

The generated color is then matched to a known substance by comparing the generated color characteristics utilizing a color algorithm. This algorithm may assess the color magnitude or intensity, rate of color change, decreasing color change and timing of the various color changes or combinations thereof. This results in the detection and/or identification of the substance.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method for detecting a substance, said method comprising:

collecting the substance on a sample medium, wherein the sample medium is impregnated with a solid test chemical comprising zinc;

wherein the solid test chemical is dispersed uniformly on a surface of the sample medium;

wherein the substance comprises an inorganic nitrate;

applying at least one liquid reagent to the sample medium;

initiating a reaction of the substance with the solid test chemical on the sample medium to generate a color, wherein the zinc reacts with the inorganic nitrate to produce nitrite ions that react with the at least one liquid reagent to produce a colored azo dye; and wherein the color corresponds to the substance.

2. The method of claim 1, wherein the solid test chemical further comprises a component selected from the group consisting of metals, transition metals, metalloids, and combinations thereof.

3. The method of claim 1, wherein the substance further comprises a component selected from the group consisting of biohazards, toxins, radioactive materials, narcotics, explosives, and combinations thereof.

4. The method of claim 1, wherein the substance comprises explosives.

5. The method of claim 4, wherein the explosives further comprise a compound selected from the group consisting of nitroaromatics, nitrate esters, nitramines, chlorates, peroxides, perchlorates, and combinations thereof.

6. The method of claim 1, wherein the substance is present on the sample medium in amounts ranging from about 10 ng to about 100 mg.

7. The method of claim 1, wherein the substance is present on the sample medium in amounts ranging from about 100 ng to about 1 mg.

8. The method of claim 1, wherein the substance is in solid state, liquid state, gaseous state, and combinations thereof.

9. The method of claim 1, wherein the substance is collected on the sample medium by swiping the sample medium onto a surface containing the substance.

10. The method of claim 1, wherein the substance is collected on the sample medium by dropping a liquid containing the substance onto the sample medium.

11. The method of claim 1, wherein the substance is collected on the sample medium by exposing the sample medium to a gaseous environment containing the substance.

12. The method of claim 1, wherein the sample medium is selected from the group consisting of filter papers, porous sheets of fibers, porous papers, and combinations thereof.

13. The method of claim 1, wherein the sample medium comprises a pad of a flexible card component.

14. The method of claim 13, wherein the flexible card component comprises at least one liquid reagent in at least one reagent releasable capsule, wherein the reaction is initiated after coupling the flexible card component with a hand held chemical detection unit, and wherein the coupling of the flexible card component with the hand held chemical detection unit causes a wall of the at least one reagent releasable capsule to yield to fluid flow to establish fluid communication between the at least one liquid reagent in the at least one reagent releasable capsule and the pad.

15. The method of claim 14, wherein the establishment of the fluid communication between the at least one reagent releasable capsule and the pad comprises a disruption of a wall of the at least one reagent releasable capsule upon the coupling of the pad with the hand held chemical detection unit.

16. The method of claim 15, wherein the disruption of the wall of the at least one reagent releasable capsule comprises an application of pressure to the wall, an application of heat to the wall, a mechanical breaking of the wall, a mechanical puncturing of the wall, or combinations thereof.

17. The method of claim 14, further comprising a step of stimulating the reaction of the substance with the solid test chemical, wherein the stimulating occurs inside the hand held chemical detection unit to generate the color that corresponds to the substance.

18. The method of claim 17, wherein the stimulating comprises an application of heat to the pad to enhance the reaction.

19. The method of claim 14, further comprising a step of utilizing an optical instrument in the hand held chemical detection unit to detect the color.

20. The method of claim 19, further comprising a step of matching the color with color of known substances in a database to determine the substance in a sample.

21. The method of claim 20, wherein the matching comprises utilizing a comparison algorithm.

22. The method of claim 20, further comprising a step of displaying detection results on a display unit of the hand held chemical detection unit.

23. The method of claim 1, wherein the reaction is initiated by incubating the sample medium at room temperature.

24. The method of claim 1, wherein the initiating of the reaction is performed in a controlled sequence of reactions with liquid reagents in at least a first reagent releasable capsule and a second reagent releasable capsule, wherein the first reagent releasable capsule and the second reagent releasable capsule are in fluid communication with the sample medium.

25. The method of claim 24, wherein the initiating of the reaction is controlled by controlling flow times of the liquid reagents in the first and second reagent releasable capsules onto the sample medium.

26. The method of claim 25, wherein the controlling comprises controlling flow rates of the liquid reagents in the first and second reagent releasable capsules onto the sample medium.

27. The method of claim 25, wherein the controlling comprises controlling arrival of the liquid reagents in the first and second reagent releasable capsules onto the sample medium.

28. The method of claim 25, wherein the controlling results in arrival of the liquid reagent in the first reagent releasable capsule onto the sample medium prior to arrival of the liquid reagent in the second reagent releasable capsule onto the sample medium.

29. The method of claim 25, wherein the controlling results in arrival of the liquid reagent in the second reagent releasable capsule onto the sample medium prior to arrival of the liquid reagent in the first reagent releasable capsule onto the sample medium.

30. The method of claim 25, wherein the controlling results in simultaneous arrival of the liquid reagents in the first and second reagent releasable capsules onto the sample medium.

31. The method of claim 1, wherein the solid test chemical is dispersed uniformly on a surface of the sample medium in a form of at least one uniform circle.

32. An assembly for detecting a substance, wherein the assembly comprises:
   a sample medium;
   a solid test chemical comprising zinc, wherein the sample medium is impregnated with the solid test chemical;
   wherein the solid test chemical is dispersed uniformly on a surface of the sample medium; and
   at least one reagent releasable capsule operable to be in fluid communication with the sample medium, wherein the at least one reagent releasable capsule comprises at least one liquid reagent;
   wherein the sample medium is configured to collect a substance thereon, and wherein the zinc is configured to react with an inorganic nitrate in the substance to produce nitrite ions that react with the at least one liquid reagent to produce a colored azo dye when fluid communication is established between the at least one liquid reagent in the at least one reagent releasable capsule and the sample medium.

33. The assembly of claim 32, wherein the solid test chemical further comprises a component selected from the group consisting of metals, transition metals, metalloids, and combinations thereof.

34. The assembly of claim 32, wherein the sample medium is selected from the group consisting of filter papers, porous sheets of fibers, porous papers, and combinations thereof.

35. The assembly of claim 32, wherein the sample medium comprises a pad of a flexible card component.

36. The assembly of claim 32, wherein the solid test chemical is dispersed uniformly on a surface of the sample medium in a form of at least one uniform circle.

* * * * *